United States Patent
MacFarlane et al.

(10) Patent No.: US 6,672,157 B2
(45) Date of Patent: Jan. 6, 2004

(54) POWER TESTER

(75) Inventors: Pamela MacFarlane, Dekalb, IL (US); Mary Visser, Maukato, MN (US); Clifford Mirman, Dekalb, IL (US); Ragu Athinarayanan, Cape Girardeau, MO (US)

(73) Assignee: Northern Illinois University, DeKalb, IL (US)

( * ) Notice: Subject to any disclaimer, the term of this patent is extended or adjusted under 35 U.S.C. 154(b) by 52 days.

(21) Appl. No.: 10/115,190

(22) Filed: Apr. 2, 2002

(65) Prior Publication Data

US 2002/0139185 A1 Oct. 3, 2002

Related U.S. Application Data

(60) Provisional application No. 60/280,821, filed on Apr. 2, 2001.

(51) Int. Cl.$^7$ ............................................. A61B 5/22
(52) U.S. Cl. ............................................. 73/379.01
(58) Field of Search ........................ 73/379.01, 379.02, 73/379.03, 379.06, 379.07, 379.08, 379.09

(56) References Cited

U.S. PATENT DOCUMENTS

| | | | |
|---|---|---|---|
| 3,465,592 A | | 9/1969 | Perrine |
| 3,848,467 A | | 11/1974 | Flavell |
| 4,235,437 A | | 11/1980 | Ruis et al. |
| 4,337,050 A | | 6/1982 | Engalitcheff, Jr. |
| 4,367,752 A | * | 1/1983 | Jimenez et al. ............. 600/502 |
| 4,601,468 A | | 7/1986 | Bond et al. |
| 4,628,910 A | | 12/1986 | Krukowski |
| 4,691,694 A | | 9/1987 | Boyd et al. |
| 4,711,450 A | | 12/1987 | McArther |
| 4,768,783 A | | 9/1988 | Engalitcheff, Jr. |
| 5,740,813 A | * | 4/1998 | Ogata et al. ................. 600/546 |
| 6,056,670 A | * | 5/2000 | Shu et al. ....................... 482/4 |
| 6,231,481 B1 | * | 5/2001 | Brock ........................... 482/8 |
| 6,308,565 B1 | * | 10/2001 | French et al. ............ 73/379.04 |

OTHER PUBLICATIONS

Adams, Gene M., *Exercise Physiology Laboratory Manual, Third Edition*, (Vertical Jump Power), 76 (1998).

Bassey EJ., et al., "A new method for measuring power output in a single leg extension: feasibility, reliability and validity," *Eur. J. Appl Physiol*, 60:385–390 (1990).

Bassey E., et al., "The effect of limb joint angles on the extensor power output of the leg in man," *J. Physiol* 420:51P (1990).

Bassey, EJ., et al., "A comparison between power output in a single leg extension and in weight–bearing activities of brief duration such as stair running in man," *J. Physiol.*, 427:12P (1990).

Bassey EJ., et al. "Leg extensor power improves in women with feasible exercise programs," *J. Physiol.*, 467:121P (1993).

* cited by examiner

*Primary Examiner*—Max Noori
(74) *Attorney, Agent, or Firm*—Kohn & Associates, PLLC

(57) ABSTRACT

There is provided a method of testing power in an individual by measuring the amount of time it takes to move an object from one location to a second location and calculating the power based on the time it took to move to object. Also provided is a power tester including a sensor device for sensing movement of a weight between at least two points, measuring device for measuring time for weight to move between at least two points, and a calculating device for automatically calculating power based upon the measurements.

9 Claims, 6 Drawing Sheets

POWER TESTER

CROSS REFERENCE TO RELATED APPLICATIONS

This application claims the benefit of priority under 35 U.S.C. Section 119(e) of U.S. Provisional Patent Application No. 60/280,821 filed Apr. 2, 2001, incorporated herein by reference.

BACKGROUND OF THE INVENTION

1. Field of the Invention

The present invention relates to a power tester for testing reaction time and muscular power. More specifically, the present invention relates to a portable power tester which can be used to determine muscular power.

2. Description of Related Art

Rehabilitation specialists are often asked to conduct an assessment of patients that have acquired a limitation to their optimal independent activity. Although the parameters of human performance vary widely, one may identify several principles which are common to all forms of independent activity. Such common principles are muscular strength, endurance, joint range of motion, and motor coordination. It is these parameters of performance that the rehabilitation specialist focuses upon. The specialist directs attention to identified parameter's which are limiting performance and evaluates the degree of the limitation.

Historically, the rehabilitation specialist has a hands on approach using his own healthy limb to resist the movement of the patient's limb. In this way, the clinician evaluates the patient's performance through feel and, at the same time, offers exercise to the limited muscle group. By repetitive hands on accommodating exercise, the limited muscle group is overloaded and adapts biologically with improved performance.

Muscle strength is a performance parameter which is quite plastic and quickly adapts to immobilization or disuse as well as to increased activity or overuse. That is, muscle strength quite quickly increases or decreases with respect to use or disuse. Disuse, such as immobilization following injury or casting after surgery, results in a significant decrease in muscle size and muscle strength. In contrast, if free weight lifting is used as the method of choice for the rehabilitation therapy, the end result is a quick response of increased muscle cell size and gain in muscle strength.

Weight lifting equipment overloads a muscle group by using gravity against which a muscle must move the weight. With free weights, no controls are present to direct the speed of movement of the limb nor the resistance throughout the range of motion that the muscle must work against. The maximum free weight resistive load that can be applied to a limb is determined by the capacity of the associated muscle group as measured throughout the range of motion of the limb. The maximum load that the limb can support varies throughout its range of motion where at some point it is at a minimum and at another it is at a maximum. Hence, the maximum resistive free weight load that can be applied is equal to the maximum supportable load in the weakest area of the range of motion.

Conventional methods of subjective assessment and reconditioning, such as subjective "through the clinician's hands" evaluations and free weight exercise, are now reinforced with technology.

Technology has been developed which provides for assessment and reconditioning of muscular deficiencies by electronic control of the rate of movement of the limb. The rate of movement control is achieved by constantly varying the amount of resistance offered the moving limb throughout the range of motion. This category of devices allow the muscle group, usually a whole limb or limb segment, to accelerate to a pre-selected speed. These constant speed devices use the methods of isokinetic or accommodating resistance.

Isometric assessment of muscular strength has been employed extensively in orthopedic, sports, rehabilitation, and industrial clinics for more than 40 years. Isometric testing typically involves a maximum voluntary contraction at a specified joint angle or functional position against an unyielding pad or handle connected to a force measuring device. In contrast to isometric testing, isokinetic testing measures strength throughout a range of motion of a body segment using a yielding, constant velocity device to which a force measuring device is attached. The isometric testing modality has become more popular due to the availability of testing products.

The first generation of isometric testing devices was developed in the early 1980s and involved measurement of only the maximal force using a cable tension meter or dial gauge. The disadvantages of these systems include the ability to measure only gross large forces, poor sensitivity at small forces, and an inability to dynamically measure forces. Additionally, the cable systems were cumbersome, setup times were long, and the number of muscle groups that could be tested was severely limited.

The second generation of these isometric testing devices used computerized testing platforms with a chair utilized for upper and lower extremity bilateral testing, spine evaluations, and lifting assessments. These systems analyzed the force curve over time, provided feedback on cogwheeling, measured fatigue, determined rate of contraction, assessed consistency of effort, calculated averages, determined bilateral deficit, etc., all related to the performance of a patient.

One disadvantage of the above-described devices is the non-integrated test chair. The chairs included in these devices were added as an afterthought. The chairs used considerable floor space due to their size, were heavy, and were wheeled or carried into place over the platform for use. In addition, the patient was removed from the chair and the chair moved several times during most exams, making the exam longer and more involved.

Another disadvantage of the above described devices is that the load cell operates in tension only, requiring multiple setups for antagonist/agonist testing. In order to provide assessments of antagonist/agonist muscle groups, cumbersome cables or straps must be used. After testing the agonists, the patient and chair must be turned around to keep the load cell in tension to test the antagonists, which increases the setup and documentation time considerably. For example, when measuring the biceps, the handle, cable, and transducer are pulled to place them in tension. When measuring the opposite motion (elbow extension using the triceps), however, the patient and chair are turned around to keep the cable/strap in tension. This requires two different setups for the chair and patient. In addition, moving in and out of the chair for every test may prove even more time consuming, burdensome, and painful for injured patients.

A further disadvantage with these above described devices is that they use two-dimensional positioning to orient the load cell with respect to the muscle group being tested, requiring complex bilateral testing setups. The positioning methods of most systems include adjustment of the load cell height, load cell angle in the vertical plane, horizontal distance from the load cell acting point, chair orientation, etc. But in most systems, the direct line of action between the plane of movement of the muscles being tested and the centerline of the transducer results in large errors in maximal force. For example, during a knee flexion test, the patient is seated in a chair and a strap is connected around the leg just above the ankle. The tranducer is lowered so the strap is horizontal. When the patient is seated in front of the transducer, the line of action is 24 degrees resulting in a strength measurement error of approximately 10 percent.

In view of the above disadvantages, there is a need for a device which provides for more convenient and accurate bilateral testing. In order to solve this problem, some devices move chair and the patient, to the right for left side testing and to the left for right side testing. This cumbersome procedure equalizes the line of action for the muscles being tested and the tranducer, but the patient is required to exit the chair, the chair is moved, and the patient is then repositioned on the chair. If multiple tests are required, the problem is compounded. Thus, there is a need for a more convenient device for bilateral testing. In addition, there is a need for a device that provides a direct line of action between the transducer and the point line of action.

Prior art devices have decreased repeatability of the tests due to the use of cables and straps. The use of cables and straps makes it difficult to position the patient exactly the same for follow-up tests. There is a need for a device that eliminates straps and cables to improve the repeatability of follow-up tests.

The above described prior art devices are unable to meet clinical requirements for functional diagnostic testing or post offer employee testing. Functional diagnostic testing in clinical environments requires a device that may be quickly customized for testing. Post-offer employee testing requires objective, baseline, tester independent, easy to administer, standard, and job specific isometric strength tests. Current devices were not designed for these emerging uses. There is still a need for a device that can be quickly customized for different tests and provide objective and easily administered tests.

In the isokinetic system, once the moving limb achieves the selected speed, the device then offers the muscle group an accommodating resistance which is proportional to the contractile force such that the limb continues to move at the selected speed. These mechanisms usually have some form of position/time feed back, servo loop which directs the resistance, for example, through feeding a variable current to a DC servo motor, such that, no matter what constantly varying force is executed by the contracting muscle group, the limb does not exceed or fall below the speed selected.

The goal with isokinetic systems is that throughout the entire range of motion of the limb, the associated muscle groups are working at their utmost level while receiving an optimal overloading resistance.

The contractile effort of a muscle group against this type of microprocessor based resistance is registered by the system and produces a profile of contractile performance which is widely recognized as accurate and repeatable. The data from such a system can be used in a court of law as evidence in disability claims.

Examples of such isokinetic systems are the Cybex, manufactured by Lumex, U.S. Pat. No. 3,465,592, inventor J. Perrine; the LIDO manufactured by U.S. Pat. No. 4,601, 468; inventor M. Bond, KIN COM manufactured by Chattanooga, U.S. Pat. No. 4,711,450, inventor J. McArther; the Biodex, U.S. Pat. No. 4,628,910, inventor R. Krukowski and U.S. Pat. No. 4,691,694, inventor R. Boyd, et al.; and the devices disclosed in U.S. Pat. Nos. 3,848,467 and 4,235,437. Each of these systems use the method of isokinetic resistive exercise/assessment applied to the large muscle groups of the legs particularly the knee.

Attachments are also available to modify these devices to address the arms and, secondarily, the ankles, wrists, and hands. With respect to the hands, gross movements are allowed by these systems which include an attachment which simulates the grip motion one would use with pliers and an attachment which has a moving rod element, with the firearm rigidly fixed, for simulation of certain wrist activities. In each case, a specific work task is simulated with these accessories.

The shortcoming of these devices is that the movements described by the hand are those which are seen specifically at job sites or only rarely in life. Reliability of the assessment data is questionable with these systems due to the inability to accurately reproduce the same posture and set up for each trial. These devices are best suited to exercise muscle groups and areas of muscle groups. The assessment aspect of these devices is severely limited by the design.

Other devices have been developed with similar intentional designs limiting the use of the system to simulations of specific work tasks. For example, U.S. Pat. Nos. 4,337, 050 and 4,768,783 issued to Engalitcheff, Jr. disclose a method and apparatus for rehabilitating injured muscles. The Engalitcheff, Jr. patent discloses an apparatus which includes a number of specific accessory elements simulating various tools coupled to a controlled resistance device. These accessories allow the therapy to address the particular work tasks an individual may be expected to perform. Each accessory element is specifically adapted to the resistance device, which includes a rotatable shaft, controlled, in one embodiment, by an electric brake coupled to an adjustable voltage source. Ostensibly, selective resistance is provided to each of the variety of various accessories to permit exercise of specific muscles or joints in simulated industrial applications. Feedback regarding the amount of force applied to each particular exercise is provided by a voltmeter; no other type of data feedback is provided.

A more sophisticated rehabilitation system, which also includes means for evaluating muscle degradation, is the LIDO.RTM. WorkSET that is manufactured by Loredan Biomedical, Inc., Davis, Calif. The Loredan device includes an adjustable resistance head, to which a number of accessories may be coupled, and various other tool-type accessories for simulating work-related activities. The resistance head generally includes a gear reducing element and a D.C. servo motor, appropriately sized to provide resistance for the various tool accessories. A personal computer controls the resistance applied to all accessories of the system, providing variable resistance to each of the accessories attached thereto for a series of exercise and evaluation modes. The Loredan system is capable of automatically implementing three general types of exercise for a test subject: isokinetic; isotonic; and isometric exercise. The isokinetic exercise mode generally provides a variable force against the particular motion undertaken by the subject, with the exercise accessory, to maintain a constant velocity on the test subject's action. The isotonic exercise mode provides a constant force against the test subject's actions to allow the subject to move the accessory device at varying speeds. The isometric exercise mode deals generally with the static measurement of the flexing and extension of particular muscles, including both concentric and eccentric contractions.

The Loredan system requires a physical floor space area of approximately 8' by 8', generally making it suitable only for large scale rehabilitative efforts. The numerous attachments are adaptable to allow rehabilitation of many muscle groups in a manner similar to the of the Engalitcheff, Jr. patent devices.

It would be useful to provide a system for the comprehensive evaluation of muscles of the body.

SUMMARY OF THE INVENTION

According to the present invention, there is provided a method of testing power in an individual by measuring the amount of time it takes the individual to move an object from one location to a second location and automatically calculating the power based on the time it took to move to object. Also provided is a power tester including a sensor device for sensing movement of a weight between at least two points, measuring device for measuring time for weight to move between at least two points, and a calculating device for automatically calculating power based upon the measurements.

DESCRIPTION OF THE DRAWINGS

Other advantages of the present invention are readily appreciated as the same becomes better understood by reference to the following detailed description when considered in connection with the accompanying drawings wherein.

DETAILED DESCRIPTION OF THE INVENTION

The present invention provides a power tester, generally in shown at 10, that assesses reaction time and muscular power. The power tester 10 of the present invention is particularly useful during weight lifting. The power tester 10 is portable and can be used with any weight lifting equipment or isokinetic testing equipment, generally shown at 69.

Figure 4:
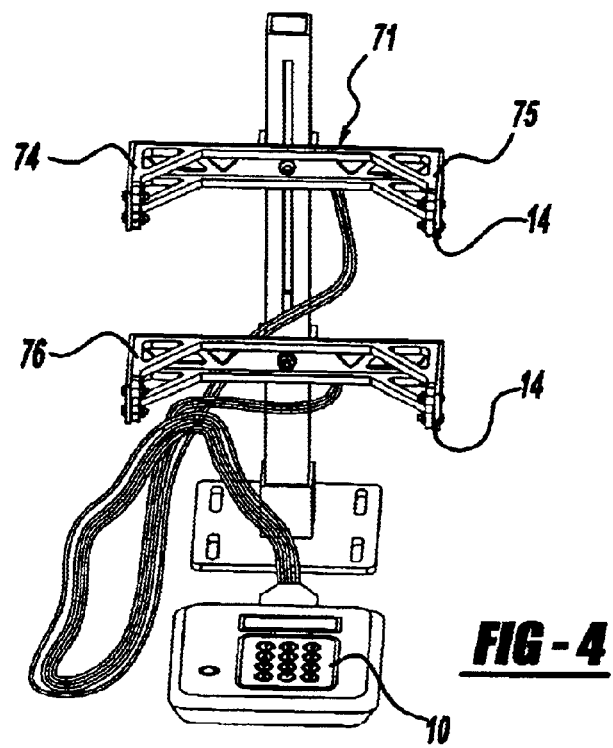
FIG. 4 is a top view of the apparatus of the present invention.
Figure 5:
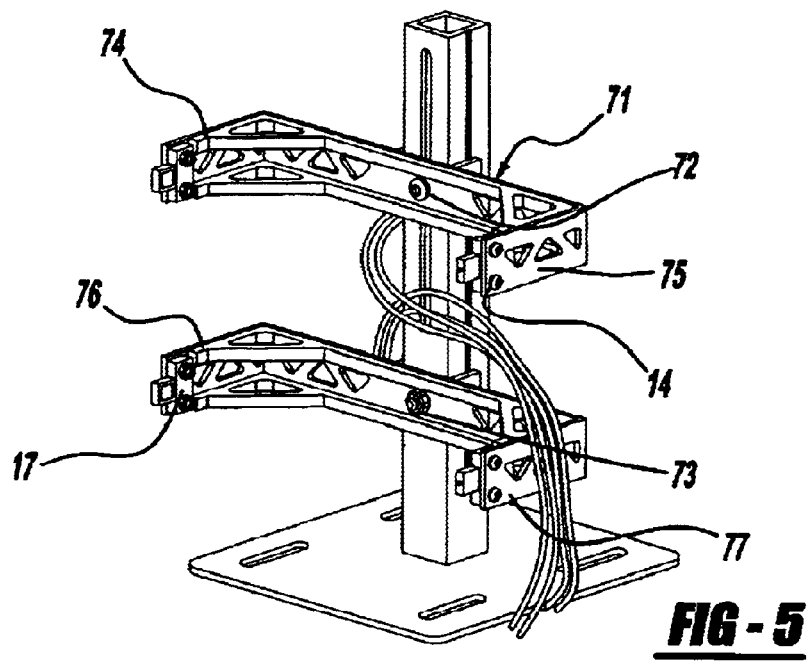
FIG. 5 is a partial side view of the apparatus of the present invention.

More specifically, the power tester 10 is a portable device that measures reaction time and the power exerted while moving any mass under resistance (FIGS. 4 and 5). The power tester 10 is preferably a hand-held micro-controller board. The power tester 10 can also include a visual and/or auditory cue 12 to signal for the subject to initiate the movement. Two electronic sensors 14, 15 detect movement of an object. The power tester 10 can then measure the time an object takes to move from sensor 14 to sensor 15, and a dual readout shows the time elapsed from cue signal to movement initiation, and the time for the mass to move from sensor 14 to sensor 15 (or power output if entering weight and distance data).

In the preferred embodiment, the power tester 10 is portable or hand held and includes an energy device. The energy device can be batteries or any other energy device, including an AC/DC connection through an electric cord. Alternatively, the instrument can be placed either inside a machine 69 or affixed to the exterior of a machine 69. Examples of such machines include the machines disclosed in the Background of the invention or other applicable machines known to those of skill in the art.

The cueing device 12 is an cue which can be given an individual. An example of such a cue is a visual signaler. The visual signaler is preferably portable such that it can be positioned in front of the subject using the machine 69 while a timing device is positioned behind the subject. Alternatively, a device can be created wherein the individual places himself in a particular location such that the visual signal can be seen from the individual's position.

The sensors 14, 15 of the present invention are triggered by movement. The sensors can be any sensors 14, 15 known to those of skill in the art which are able to detect movement. The sensors 14, 15 can detect movement through the use of trigger 17, which when set off, indicates movement. The trigger 17 is any apparatus which enables the sensors 14, 15 to detect movement. For example, the trigger 17 can include a photo sensor emitting beam, a beam of light, which when there is an interruption in the beam, indicates movement or other similar devices that can detect movement. The trigger 17 can also be a mechanical device such as whiskers protruding from the instrument, an electronic sensitive eye reflector placed within the mass or resistance, or any other such trigger known to those of skill in the art.

Figure 6:
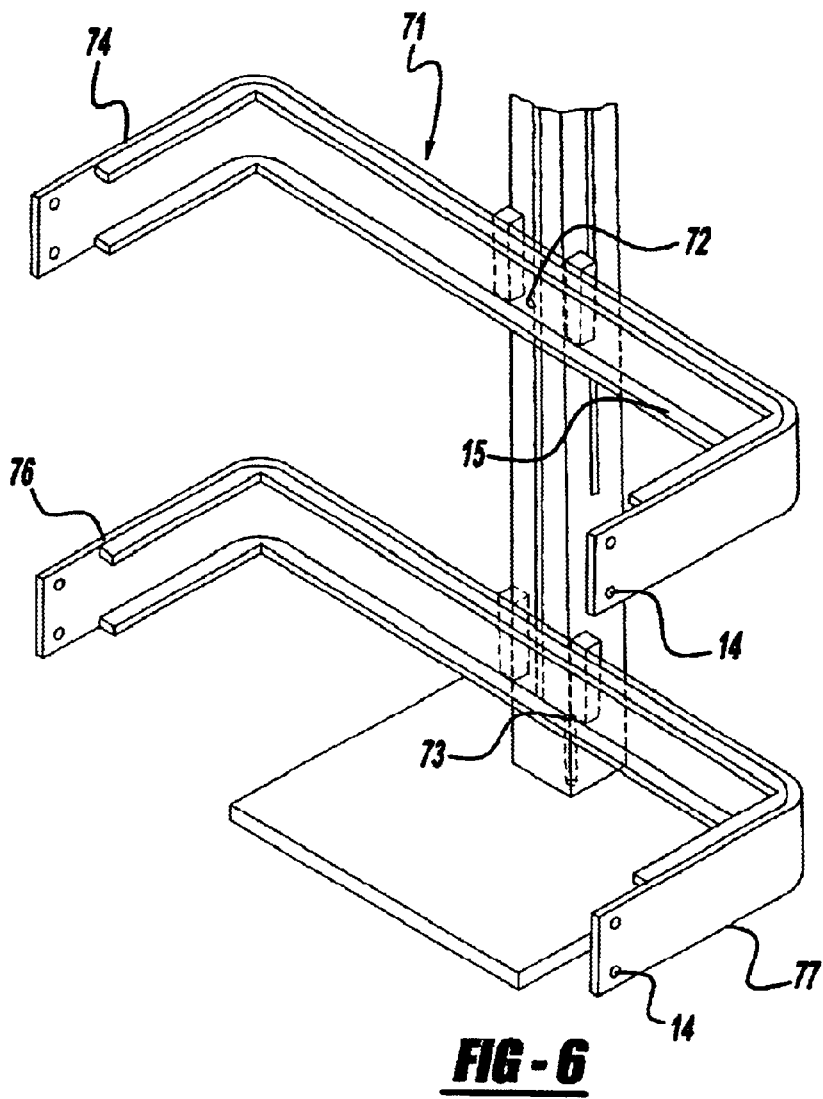
FIG. 6 is a schematic of the apparatus of the present invention.

Preferably the sensors 14, 15 are infrared photo-detector/receivers that are mounted horizontally on a rigid frame 71. The frame 71 (FIG. 6) is adjustable, allowing alteration in the distance between the sensors 14, 15. The frame 71 is mounted on a tripod 72 so the lower pair of sensors 14, 15 is just above the mass to be moved. The frame 71 is preferably made of a solid metal such that the frame 71 can withstand movement while holding the sensors 14, 15. The frame 71 height is adjustable using a series of holes 72, 73 is the frame 71. The holes 72, 73 allow the frame 71 to adjust in height while maintaining proper support for the sensors 14, 15. The frame 71 has at least two pairs of arms 74, 75 and 76, 77. The pairs of arms 74, 75 and 76, 77 maintain the sensors 14, 15 in proper alignment. The distance between the arms 74, 75 and 76, 77 is sufficient to enable a mass to pass therebetween.

Generally, the power tester 10 of the present invention can be used in conjunction with any isokinetic or isometric machines 69.

Figure 1:
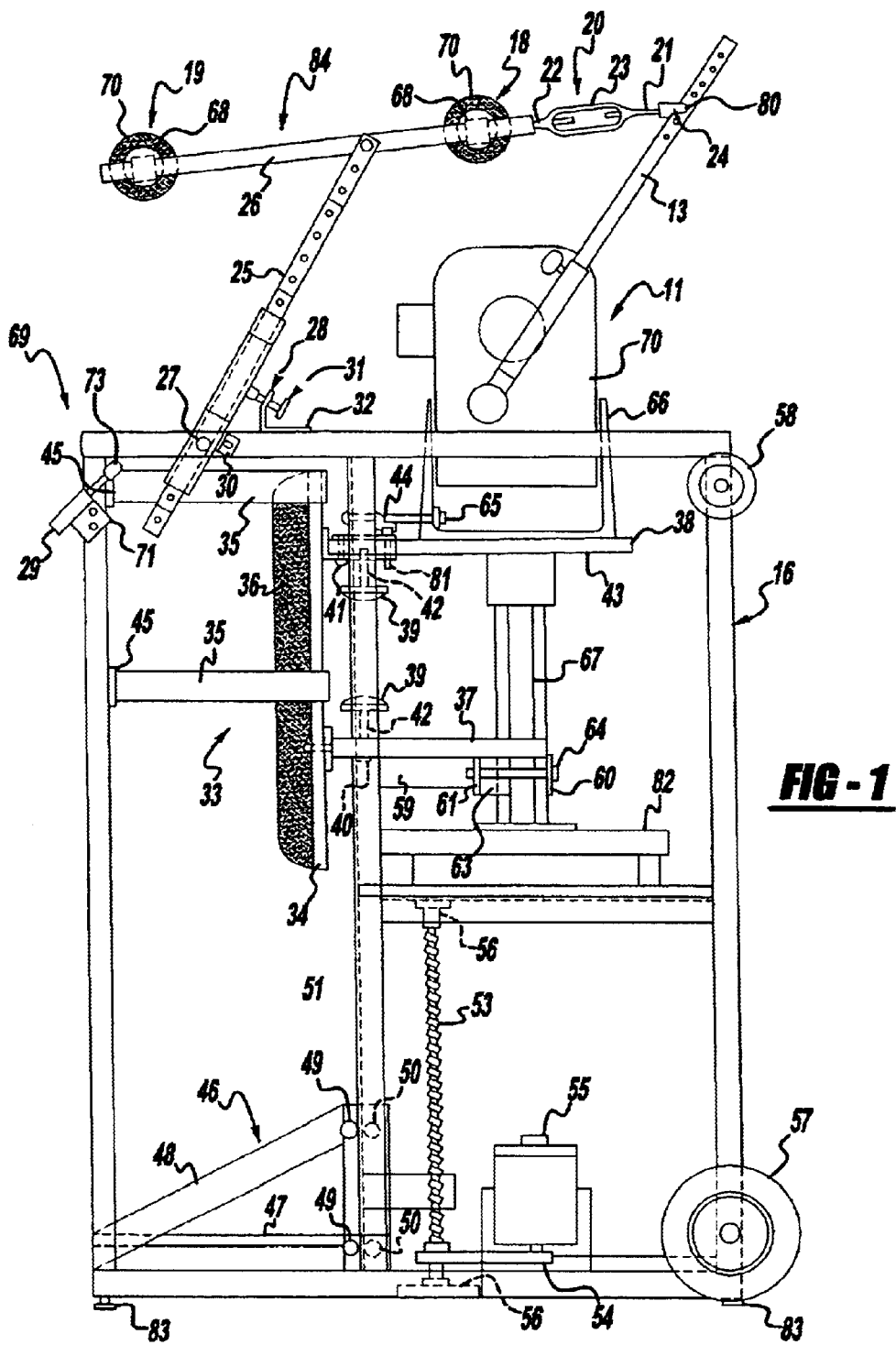
FIG. 1 is a side elevational view of a preferred embodiment of the machine.

FIG. 1 illustrates a side elevational view of a preferred embodiment of the machine 69. A dynamometer, indicated generally with the reference numeral 11, has a base 65 and a lever arm 13. Mechanical or hydraulic isokinetic dynamometers can be used. The electromechanical type of dynamometer is preferred because of the ease of instrumenting it to set a predetermined speed and of determining the torque output as discussed below. One aspect of the invention is particularly directed to the type of dynamometer shown in FIG. 1. Twisting of the lever arm 13 can be minimized by attaching the lever arm 13 to a particular point of the upper body restraint means as also discussed below.

The dynamometer base 70 is further supported by a dynamometer support yoke 66 attached to a dynamometer pedestal 67.

The machine 69 includes a support frame 16 to which the dynamometer base 70 is fixedly attached as discussed below.

It should be noted that the dynamometer base 70 could also simply be attached to the floor or other substantially immovable object.

The dynamometer lever arm 13 is connected to an upper body restraint assembly, indicated generally with the reference numeral 84. The upper body restraint assembly 84 includes a rear crosspiece assembly 18 and a front crosspiece assembly 19, with the crosspiece assemblies 18 and 19 preferably covered with a resilient material as discussed below. The front crosspiece assembly 19 is adapted to engage the front surface of an individual's upper body while the rear crosspiece assembly 18 is adapted to engage the back surface. A turnbuckle assembly 20 is pivotally interposed between the dynamometer lever arm 13 and the rear crosspiece assembly 18. The turnbuckle assembly 20 includes a rear link rod 21 and a front link rod 22. The link rods 21 and 22 preferably include male threads substantially along their entire lengths. The male threads on the link rods 21 and 22 have opposite senses; if the thread on link rod 21 is right handed, then the thread on link rod 22 is left handed and vise versa. The turnbuckle 23 includes female threaded openings suitable for engaging the threaded link rods 21 and 22. When the turnbuckle 23 is axially rotated in a first direction, the link rods 21 and 22 approach one another. When the turnbuckle 23 is axially rotated in a second direction, the link rods 21 and 22 move away from one another. This permits the free end of the dynamometer lever arm 13 to be moved with respect to the rear crosspiece assembly 18 during set-up of the machine 69 to better accommodate an exercising individual. The rear link rod 21 is pivotally attached to the dynamometer lever arm 13 by a link rod pivot member 24 that operatively engages the rear link rod 21 and the dynamometer lever arm 13. The link rod pivot member 24 preferably includes a female threaded hole at one end suitable for threaded engagement with the rear link rod 21. The link rod pivot member 24 is substantially U-shaped at the other end so that it can straddle the lever arm 13, and the pivot member 24 preferably includes holes that can be aligned with holes on the dynamometer lever arm 13, and a pivot bolt 80 is placed therethrough to provide another means for adjusting the machine 69.

The upper body restraint assembly 84 is preferably pivotally connected to the support frame 16 by a swing arm 25 that is fixedly connected, preferably welded, to an interconnection link 26 that provides a connection between the crosspiece assemblies 18 and 19 and holds them in parallel relationship therebetween. A pivotable connection is provided between the support frame 16 and the swing arm 25 by a pivot bolt 27 through the swing arm 25 and support frame 16. The pivot bolt 27 can be removed so that another hole in the swing arm 25 can be aligned with the corresponding hole in the frame 16 so that the swing arm can be effectively lengthened or shortened.

The machine 69 further includes three means for limiting the travel of the upper body restraint assembly 84 and swing arm 25 as the individual flexes and extends his back muscles. A pair of forward stops 29 limit movement in one direction while rearward upper stops 28 and rearward lower stops 30 limit movement in the opposite direction. The rearward upper stops 28 each comprise a male threaded bumper 31 and a female threaded bumper bracket 32, thereby allowing adjustment of the rearward travel of the upper body restraint assembly 84 by advancing or retracting the threaded bumper 31.

The lower body of the exercising individual is restrained by a lower body restraint assembly, indicated generally at 33. The lower body restraint assembly 33 preferably includes a wooden back board 34 and nylon straps 35. Further, the back board 34 is covered on its front side with a back board cushion 36 against which the back surface of the individual's lower body makes contact while the individual is utilizing the isokinetic exercising and monitoring machine 69.

The lower body restraint assembly 33 also includes means for horizontal adjustment. On the rear substantially planar surface of the back board 34 are attached a lower back board adjustment member 37 and a pair of upper back board adjustment members 38. The adjustment members 37 and 38 are substantially perpendicular to the back board 34 and are adapted to slidably engage lower adjustment bracket 40 and upper adjustment bracket 41, respectively. The adjustment brackets 40 and 41 are fixedly attached, preferably welded, to the support frame 16. The adjustment brackets have openings that admit the adjustment members 37 and 38 and allow the adjustment members 37 and 38 to freely slide therein. Hand knobs 39 attached to threaded rods 42 are in threaded engagement with the adjustment brackets 40 and 41, and when the hand knobs 39 are rotated in a clockwise direction the threaded rods 42 engage the adjustment members 37 and 38 so that the lower body restraint assembly is held in a fixed position with respect to the support frame 16. The upper adjustment members 38 and upper adjustment brackets 41 include cotter pin holes 43 and 81, respectively, that accommodate cotter pins 44 so that an even more secure attachment is provided between the lower body restraint assembly 33 and the support frame 16. Strap latches 45 permit the straps 35 to be opened so that an individual can step into the lower body restraint assembly 33 in a more convenient fashion.

The machine 69 can also include a means for vertically moving the individual with respect to the lower body restraint assembly 33 and the upper body restraint assembly 84. A platform assembly 46 is provided for this purpose.

The platform assembly 46 comprises a platform 47, preferably made of plywood, supported by a metal platform frame 48. Attached to the platform frame 48 are outside rollers 49 and inside rollers 50. The rollers 49 and 50 are preferably made of a hard metal, for example steel, and are pinned to the platform frame in any convenient fashion to permit rolling of the rollers 49 and 50. The rollers 49 and 50 are configured to pinch a roller guide 51 which is comprised of angle iron that is fixedly attached to and an integral part of the support frame 16. Operatively attached to the platform frame 48 is a driven block 52 that also engages a vertical worm gear 53. The driven block 52 includes female threads that engage the male threads on the worm gear 53 so that when the worm gear 53 is rotated about its longitudinal axis, the driven block 52 is caused to move vertically thereby also moving the platform frame 48 and the platform 47 in a vertical direction. The worm gear 53 is preferably attached to a belt 54 to an electric motor 55 so that it may be so rotated. A 3-position switch, having an off position, a clockwise position, and a counterclockwise position is preferably included with the preferred embodiment 69 so that the electric motor 55 can be properly energized to turn clockwise or counterclockwise or turned off depending on the vertical adjustment required. Thrust bearings 56 are attached to the support frame 16 and engage the worm gear 53 to allow it to rotate freely about its longitudinal axis when the electric motor 55 is energized.

In order to provide portability to a preferred embodiment of the machine 69, there are rotatably connected to the support frame 16 a pair of lower wheels 57 and a pair of upper wheels 58. The machine 69 can then be oriented so that the lower and upper wheels 57 and 58 make contact with the floor and the machine 69 can then be easily rolled from one room to another, for example. The upper body restraint assembly 84 and its attendant hardware are preferably removed or locked to the support frame 16 during this operation.

The wheels 57 and 58 are not in contact with the floor during operation of the machine 69. Attached to the frame 16 are leveling legs 83 that actually support the frame 16 during use of the machine 69. The leveling legs 83 are preferably in threaded engagement with the frame 16 so that they can be retracted and extended as needed to level the machine 69.

Figure 2:
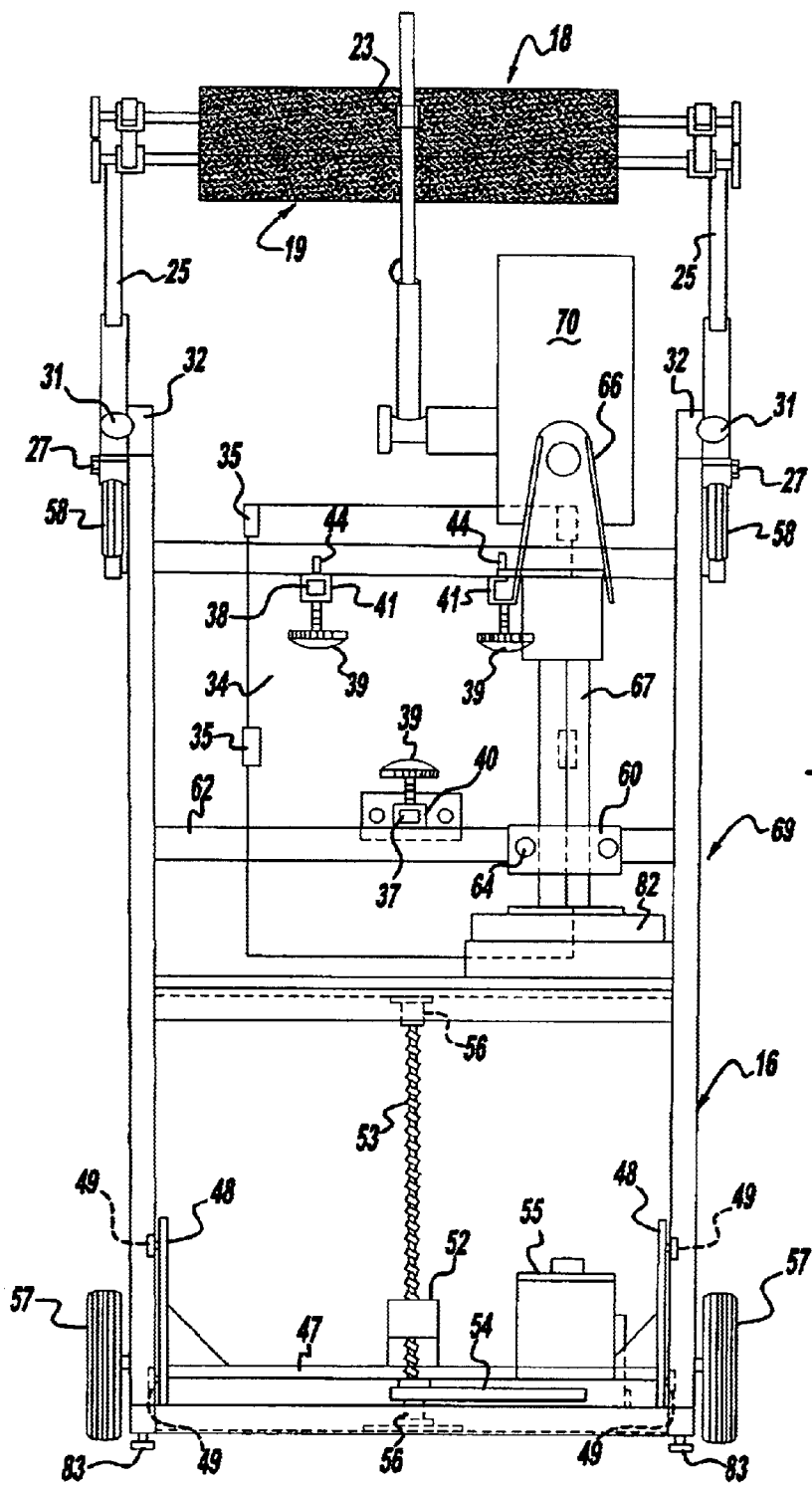
FIG. 2 is a rear elevational view of the embodiment of the invention shown in FIG. 1.
Figure 3:
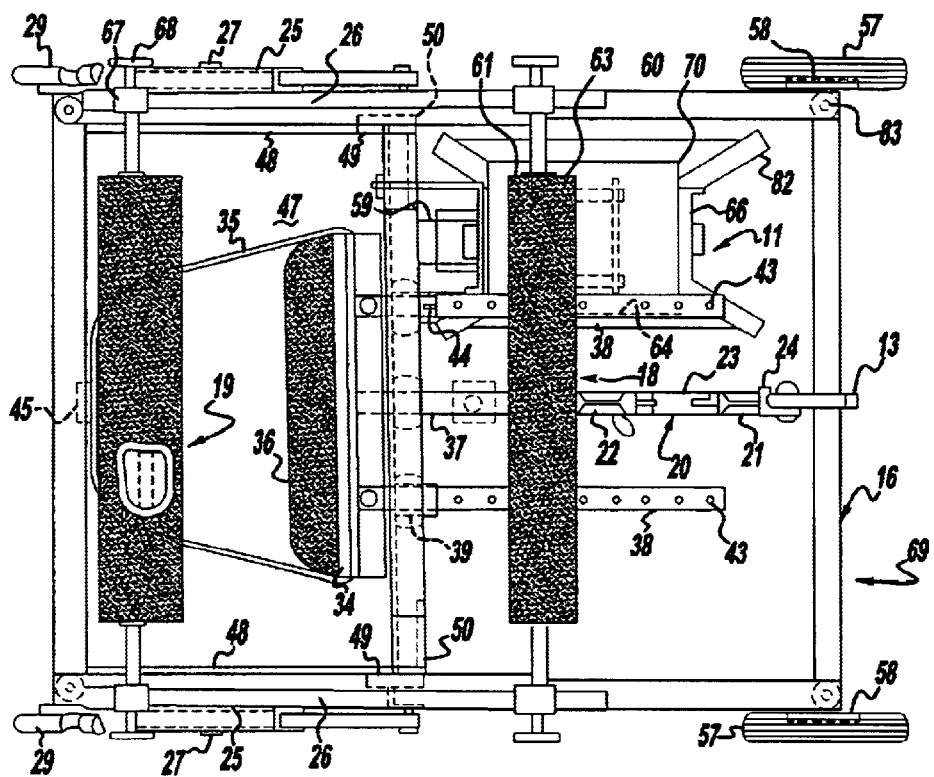
FIG. 3 is a top plan view of the embodiment of the invention shown in FIG. 1.

Still referring to FIG. 1, the dynamometer base 70 is effectively connected to the lower body restraint assembly 33 in the following fashion: the dynamometer base 70 is attached to the dynamometer support yoke 66 which is further attached to the dynamometer pedestal 67 as described above. A pedestal clamping member 59, preferably welded at one end to the support frame 16, extends from the lower horizontal member 62, as shown in FIG. 2. At the other end of the pedestal clamp member 59 there is fixedly attached an inside pedestal clamp 61 that includes two holes having female threads. The block 63, shown in FIG. 3, includes two holes having larger diameters than the holes in inside pedestal clamp 61. The block 63 is also notched to match or accommodate the shape of the dynamometer pedestal 15, as shown in FIG. 3. Pedestal clamping bolts 64 are inserted through the block 63 and are in threaded engagement with the inside pedestal clamp 61, thereby securely attaching the dynamometer pedestal 15 to the lower horizontal member 62 which is an integral part of the support frame 16. A pair of yoke bolts 65 attach the dynamometer yoke 66 to the support frame 16. The dynamometer pedestal 67 is further supported by a dynamometer platform 82 that engages the support frame 16. A rigid connection between the dynamometer base 70 in the support frame 16 is thereby effected, allowing a more accurate measurement of the torque created by the exercising individual on the dynamometer lever arm 13.

The instrument of the present invention is manufactured such that there is a variable distance between the sensors. Additionally, the instrument is able to accept the distance that is being used and then is able to calculate the power from that information (power=resistance×distance between sensor/time from sensor 1 to sensor 2). The reaction time can also be used for this calculation. As set forth above, the reaction time is the time from stimulus to initiation of movement. At a minimum, the instrument of the present invention is able to measure the time it takes for an object to move from one position to another position, a set distance away.

The ability to exert muscle power is important in the effective performance of many sport skills where the body has to change speed and/or direction quickly. Low leg extensor power has also been identified as a primary predictor of falls in the elderly. Groups such as these that span the mobility continuum benefit from accurate movement-specific assessments of power. Power testing equipment is expensive, has minimal or limited portability, and is limited to one movement. The present invention provides a power tester 10 which was developed to be a portable, relatively low cost device to measure power during a wide variety of open and closed chain movements. The power tester 10 is a portable microprocessor based device that consists of an input structure, a hand held controller, and output devices.

The present invention can be used in a situation where power output is important. The invention can therefore be used for athletes, people in rehabilitation, in the work force for work hardening programs, and for the elderly where power output has been affected because of falls.

The present invention measures both reaction time and power. Reaction time is the time it takes from the signal, either visual or auditory, to the initiation of movement. Power is either equal to work/time, work×distance, or mass×acceleration, wherein the mass is the mass being lifted and acceleration is equal to 9.81 m/sec$^2$. Therefore, power can be determined by entering the mass be lifted and the distance between sensors or any resistance used.

The present invention is useful because the assessment of power in sports and rehabilitation is important and is more closely linked to performance and general ability than strength which is most often being measured currently. Strength is currently being measured because it is easier to assess than power. However, the device of the present invention enables power to be determined based on the above calculations.

The instrument functions as follows. The user enters the mass and distance between the sensors and the subject is then cued (either audible or visual) by the controller to accelerate the mass as quickly as possible so that the mass breaks the plane of the two pairs of sensors. When both sensors are triggered the controller presents the following data: time from cue to first sensor trigger, time between sensor triggers, mean power of movement calculated from the speed of movement and the entered mass. (P=work/time=force×distance/t=f×speed=mass×acceleration×speed=mass×9.81×speed).

The above discussion provides a factual basis for the use of the power tester of the present invention. The methods used with and the utility of the present invention can be shown by the following non-limiting examples and accompanying figures.

EXAMPLES

Example 1

A prototype has been developed and preliminary data on knee extension has been collected to validate the power tester's 10 use with an isokinetic machine (KinCom 500) and a field test (the vertical jump). Eighteen subjects (12 males and 6 females, all currently active in resistance training, ages 18–36) were tested using the power tester 10 for knee extension on a standard isotonic resistance machine (1RM, 50-, 60- and 70% 1RM) and the vertical jump. Seven males and six females also completed isokinetic testing on a KinCom 500 (0-, 60-, 90- and 120°/sec).

Maximum measured power tester 10 power (best from either 50-, 60- or 70% 1RM) correlated with the strength and power measures as follows: 1RM (isotonic machine): 0.814 (p,0.0001); 120°/sec peak isokinetic power: 0.845 (p<0.0001); 120°/sec mean power for the first 30 degrees (the ROM used for the power tester 10 testing): 0.741 (p=0.004); peak vertical jump power: 0.791 (p<0.0001), and vertical jump displacement: 0.573 (p=0.013).

Results showed the power tester 10 is a valid measure of power assessment during knee extension. The instrument was easy to use and is an instrument that can be used in a clinical, exercise, home, or office setting.

The power tester 10 is useful in the assessment of power for healthy and injured athletes and is a useful screening tool to assess the risk of falls due to low leg power in the elderly who are at risk for falling.

Isokinetic machines, where the speed of an isotonic contraction is controlled while the subject exerts maximal force against a rotating lever, have been used for measuring power. Isokinetic machines are commonly found in laboratory settings, rehabilitation facilities, or in exclusive athletic facilities due to their expense. Their cost and accessibility limit their use by athletes or the elderly.

Two power devices have been developed and presented in the literature. The Omnikinetic (interactive Performance Monitoring, Inc., Pulman, Wash.) and the power rig have both been developed to assess the power of the lower extremity during a combination of closed chain knee and hip extension. The Omnikinetic was developed for use by athletes and the power rig for use by the elderly.

Power Tester Validation Using the Isokinetic Dynamometer.

Power tester 10 was used for measuring power at 50, 60, 70% 1RM for each leg separately.

First, an isotonic knee extension machine was used where the weight increments are small (5–10 pounds or you have adjustable weights that can be secured to the stack). The weight increments were secured. The start of the knee extension was at 90 degrees of flexion so the range of motion could be adjusted. With high resistances this can pose a problem, as the center pin tube can be too short. The machine was greased prior to starting, and checked to ensure that the cable was smooth.

The weight on the machine was calibrated up to about 70 Kg. To calibrate correctly the isometric dynamometer was secured to the end of the cable that was attached to the foot plate and was distal to the weight stack. The dynamometer can be attached to the shin plate at the length to be used in testing. Each varying weight, beginning with no pin through to about 70 Kg was measured. This accounted for the friction of the cable on the system.

Before testing, a chart that was made had the settings for each subject or each resistance. A calibration line was plotted based on the dynamometer weights of each plate. The appropriate number of plates or weight add-ons was calculated for 60, 70 and 80% 1RM for each plate set. A list of the weights in Kg was kept because this has to be entered into the power tester 10.

A trigger was fixed onto the top of the weight stack. A half-inch by 18-inch plastic water pipe was attached with an adjustable band that had a holder for the pipe.

Subjects were allowed to warm up using both legs at the same time. To identify the 1RM they worked from the regular ROM of the machine, not starting at 90 degrees. A 1RM was used on their weaker leg to determine the testing resistances. When they were using one leg the other leg was kept in position but pulled back.

For each resistance the pin was set in a selected weight and further weight was added if necessary. The subject raised the weights using both legs until their knees were at 90 degrees. The ROM pin was set and gummed into a position with a bit of stickup into the pin to hold it in position.

For each resistance (60, 70, 80% 1RM), the right leg was tested three times then the left leg was tested three times. This allowed sufficient rest between trials without more than three in a row to fatigue the subject. Entering the power tester 10 information and recording the data from each trial gave the subjects a good 20–30 second rest between trials.

The beep option on the tool was used with the subject holding the tool up to his or her ear. The reaction time was recorded along with the movement time and the power. The sensors were set 15 cm apart. The tool was set so that the trigger was visually placed within one centimeter of the first set of sensors.

The cable was checked to ensure that the cable was on its pulleys each time, because when you limit the ROM, the cable can pick up slack then jam up causing damage to the cable and strain to the subject. The quick acceleration at the end of the power tester 10 beep was stressed to ensure that the subject caught the weight before coming down. (With a powerful extension the weight can be launched and then smash down (and break) unless it is lowered gently onto the ROM pin.)

Subjects were allowed to hold onto the seat handles, because that is how they traditionally use the machine. During isokinetic testing the protocol tested the subjects with arms crossed on the chest but the subject was strapped into the machine using straps across the hips and chest.

The following protocol was performed but with an adjustment for speeds. Subjects were tested at 60, 90 and 120°/sec. The suggested speeds to test at are 90, 120 and 150°/sec. These speeds should include the max power level of most subjects and should overlap the speeds used in the power testing.

Protocol

Subjects warmed up on a bicycle ergometer for five minutes. A setting of three on the bike was used, which is equivalent to light or moderate resistance.

The isokinetic machine was set so that the axes of the knee and lever arm were lined up. The subject was strapped into the machine, with an ankle pad in a standardized position based on individual leg length.

The subject was given five warm up trials for each test (each speed and each leg). Subjects kept their arms across the chest and could hold onto the shoulder straps but were not allowed to hold onto the seat.

The CON/ECC mode was selected but only CON was used for testing and required exertion. ECC was accommodated with the subject pushing just hard enough to return the flexion position. Each test consisted of only one maximum exertion. For all tests the ROM was from 90 degrees knee flexion to 0 degrees of flexion (straight). Subjects had between 20 and 30 seconds of rest between exertions.

Speeds were tested from slow to fast. At each speed the subject had to match the graph at least twice for the measurement to be valid. Some subjects accomplished this in their three trials, however some took six to eight trials.

The values obtained were:

a. The length of the lever arm (distance from machine axis to ankle pad position);

b. The max force/max torque and the timer or ROM at which this occurs;

c. The average force or power during the first 30 degrees of movement (this is from 90 degree knee flexion angle until a 60 degree knee angle). An equivalent time interval would be 0.33 seconds (90°/sec), 0.25 seconds (120°/sec) and 0.2 seconds (150°/sec).

These mean values are to approximate those for the ROM used in the isotonic condition with a 15 cm timing distance on the power tester 10 set so that the lower sensors are just above the weight.

Vertical Jump.

The Vertek instrument to measure vertical jump. The jump distance was the distance between the maximum one hand reach height (while reaching from standing and able to go on tip toes) and the maximum jump height (standing jump with freedom to use arms at will and reach with one hand).

Subjects

The original subjects were men and women between the ages of 18 and 35 who were all currently in resistance training programs. Testing was at the end of a semester so the minimal time of training was 14 weeks.

Example 2

The Controller is a hand-held, battery-powered microcontroller board based on Motorola 68HC11 microprocessor. It includes 32K static RAM, 16 inputs for a variety of sensors (7 analog sensors and 9 digital sensors), two user-programmable buttons, one knob, piece-beeper, and a 16×2 character LCD screen. The Controller runs Interactive C, a cross-platform, multitasking version of the C programming language.

Ports and Connectors

Figure 7:
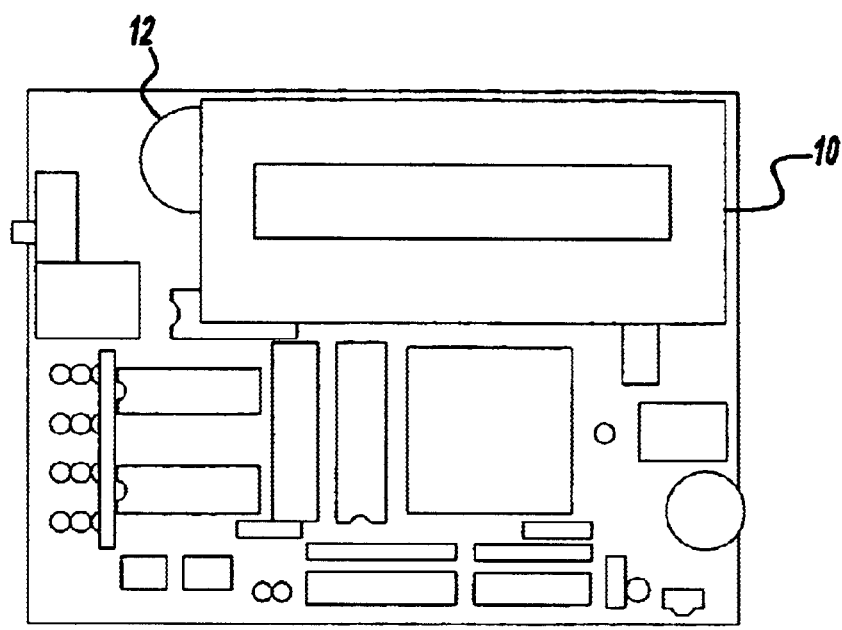
FIG. 7 is a diagram of the controller of the present invention.

FIG. 7 shows a labeled view of the Controller's ports, connectors, inputs, and outputs. The item used for the project are briefly discussed below.

Power Switch: The power is used to turn the controller on and off. The controller retains the contents of its memory even when the board is switched off.

Computer Connector: Via the RJ11 connector, the controller attaches to a computer using a separate Serial Interface board (provided).

Stop Button: The Stop button is used to put the controller into a special bootstrap download mode.

Low Battery Indicator: The red Low Battery LED lights when for a brief interval each time, the Handy Board is switched on. If the LED is on steadily, it indicates the battery is low and the CPU is halted.

Power/Ready Indicator: The green Power/Ready LED lights when the controller is in normal operation, and flashes when the controller is transmitting serial data. If the board is powered on and this LED is off, then the controller is in special bootstrap mode.

Charge indicator: The yellow charge indicator LED lights when the controller is charging via the coaxial power jack.

Setting up the Controller for Use a. Computer connection. The Serial Interface board provided in the controller package connects the controller to a computer. Using the standard 4-wire telephone cable, the Controller is connected to the Serial Interface board. A standard modem cable can be used to connect the Serial Interface board to the serial port of the computer. Upon connecting power to the Controller and appropriate LED's on both controller and the Serial Interface board both light up.

Preparing the 68HC11 for the Operation Program (Downloader Program)

The Controller is put into bootstrap download mode when using the downloader. The power is first turned OFF to the Controller. While the power is OFF, the STOP button is held down while turning on the power switch. The pair of LED's by the two push buttons light up for ⅓ of a second and then turn off. When power is on and both of the LED's are off, the Controller is in download mode. The program can then be downloaded.

Using the Controller

IC (Interactive C) is a C compiler/interpreter for use with the Controllers. At the command prompt, the appropriate C command can be typed and the RETURN button hit. This command can be executed immediately.

The following are the descriptions of commands to which IC can respond:

Load file. The command load <file name>; complies and loads the named file. IC looks both in the local directory and the IC library path for files;

Unload file. The command unload <file name>; unloads the named file;

List files, list functions, or list globals variables. The commands are list files displays all the files loaded in the Controller; list functions displays the currently loaded C functions in the Controller; and list globals displays the names of all currently defined global variables;

Kill all. The command that kills all currently running processes in the Controller;

Help. The command help displays a help screen of IC command.

Quit. The command quit exits IC.

Downloading the Control Programs

Communicate to the controller and after receiving the "C>" prompt, type the following commands to download the following programs in the order shown below. Hit the Enter Key after each command.

C>Load choice.c
C>Load time.c
C>Load keypad.c
C>Load mainl.c

After entering the commands above, cycle the power (turn power OFF and then ON) to the controller and the unit should now be ready for use.

Throughout this application, various publications, including United States patents, are referenced by author and year and patents by number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention can be practiced otherwise than as specifically described.

REFERENCES

1. Bassey E J. Measurement of muscle strength and power. Muscle and Nerve, 1997; supplement 5:S44–S46.
2. Bassey E J., Short, A H. A new method for measuring power output in a single leg extension: feasibility, reliability and validity. Eur. J. Appl Physiol, 1990; 60:385–390.
3. Bassey E., Delbridge A., Short A. The effect of limb joint angles on the extensor power output of the leg in man. J. Physiol 1990; 420:51P.
4. Bassey, E J., Tay, G., West, F. A comparison between power output in a single leg extension and in weight-bearing activities of brief duration such as stair running in man. J. Physiol 1990; 427:12P.
5. Bassey E J., Ramsdale S J. Leg extensor power improves in women with feasible exercise programs. J. Physiol 1993; 467:121P.
6. Skelton, D A., Kennedy J., Rutherford, O. Lower limb muscle power in frequently falling community dwelling women aged 65 and over. Presentation at the International Meeting of Activity and aging 1999, Orlando, Fla.
7. Adams, G M. Exercise Physiology Laboratory Manual, Third Edition, 1998, WCB McGraw-Hill Publishers (Vertical Jump Power pg 76).

What is claimed is:

1. A power tester comprising:

sensor means for sensing movement of a mass between at least two points;

measuring means for measuring time for the mass to move between said at least two points, said measuring means beginning the measurement when the mass moves past the first point and stopping when the mass moves past the second point; and calculating means for automatically calculating power based upon the measurements.

2. The power tester according to claim 1, further including cueing means for cueing said sensor means of initial movement of the mass.

3. The power tester according to claim 1, wherein said sensor means includes a trigger selected from the group consisting essentially of whiskers, a beam of light, and an electronic sensitive eye reflector.

4. The power tester according to claim 1, wherein said power tester is portable.

5. The power tester according to claim 1, wherein said power tester includes energy means operably connected to said power tester for providing energy to said power tester.

6. The power tester according to claim 5, wherein said energy means are selected from the group consisting essentially of batteries and an AC/DC connection.

7. The power tester according to claim 1, wherein said calculating means is a computer program for calculating power.

8. The power tester according to claim 1, wherein said power tester 10 includes an isokinetic machine for testing power.

9. A method of testing power in an individual by measuring the amount of time it takes to move an object from one location to a second location when the individual is cued electronically to do so, said measuring step including cuing an individual to move a mass past a first point thereby starting the measuring and stopping the measuring when the mass passes a second point, and calculating the power based on the time it took to move to object.

* * * * *